United States Patent
Namba

Patent Number: 5,993,457
Date of Patent: Nov. 30, 1999

[54] MEASUREMENT DEVICE AND METHOD FOR TOTAL HIP ARTHROPLASTY

[75] Inventor: Robert S. Namba, Irvine, Calif.

[73] Assignee: The Regents of the University of California, Oakland, Calif.

[21] Appl. No.: 09/156,040

[22] Filed: Sep. 17, 1998

[51] Int. Cl.$^6$ .................................................. A61B 17/56
[52] U.S. Cl. ............................. 606/102; 606/86; 606/87
[58] Field of Search ................................ 606/86, 87, 88, 606/89, 91, 102

[56] References Cited

U.S. PATENT DOCUMENTS

| | | | |
|---|---|---|---|
| 3,801,989 | 4/1974 | McKee | 606/86 |
| 3,815,590 | 6/1974 | Deyerle | 606/102 |
| 3,955,568 | 5/1976 | Neufeld | 606/86 |
| 5,888,211 | 3/1999 | Sanders | 606/102 |

*Primary Examiner*—Michael Buiz
*Assistant Examiner*—Daphna Shai
*Attorney, Agent, or Firm*—Richard Aron Osman

[57] ABSTRACT

Postoperative change in lower extremity length during total hip arthroplasty is controlled by determining a control distance between proximal and distal fixed reference points on a control femur, wherein the control distance provides an indication of the length of the femoral head of the control femur, and adjusting a corresponding operative distance between corresponding proximal and distal fixed reference points on a corresponding operative femur of a lower extremity in relation to the control distance. The method employs provisional femoral heads comprising a pin inserted into the axis of rotation of the head whereby when the head is installed on an operative femur, the axis of the pin is perpendicular to the axis of the femur.

11 Claims, 1 Drawing Sheet

MEASUREMENT DEVICE AND METHOD FOR TOTAL HIP ARTHROPLASTY

INTRODUCTION

1. Field of the Invention

The invention is in the field hip replacement surgery.

2. Background

Leg length inequality, specifically lengthening of the leg, is the leading cause of lawsuits following total hip arthroplasty (THA) procedures. One of the final decisions during THA surgery is to determine which length of femoral head to attach to the trunion of the implanted stem. The leading determinant in choosing a particular length of the femoral head is the stability of the artificial joint. To avoid postoperative dislocations, the lower extremity is moved to simulate positions at risk. An assessment is made of the soft tissue tension holding together the components of the newly implanted joint replacement. The length of the femoral head is chosen to maximize stability of the THA without significant changes in length of the lower extremity. A device which accurately provides a guide to whether the lower extremity length has been changed would be greatly beneficial.

Previous devices developed to measure limb length during THA procedures consist of direct measurement of implants (e.g. pins) temporarily impaled into or affixed to the pelvis and proximal femur, e.g. Gadelius, 1997 (U.S. Pat No. 5,616,147); Benson, 1997 (U.S. Pat No. 5,603,717); Fishbane, 1992 (U.S. Pat No. 5,122,145); Benson, 1994 (U.S. Pat No. 5,318,571); Benson, 1996 (WO96/40021); Chagneau, 1993 (French Pat No. 2684287); S. T. Woolson, M.D., et. al., "A Method of Interoperative Limb Length Measurement in Total Hip Arthroplasty" *Clinical Orthopaedics and Related Research*, 1985, 194:207–210; L W. H. Harris, M.D., "Revision Surgery for Failed Nonseptic Total Hip Arthroplasty" *Clinical Orthopaedics and Related Research*, 1975, 106:19–26; and N. M. J. McGee, F.R.C.S., et. al., "A Single Method of Obtaining Equal Leg Length in Total Hip Arthroplasty" *Clinical Orthopaedics and Related Research*, 1985, 194:269–270. These devices are cumbersome, may require that surrounding muscles be impaled which may loosen the pins and limit surgical exposure, and require that the lower extremity be reproducibly positioned in an identical manner during each reading to ensure proper measurement across the joint.

SUMMARY OF THE INVENTION

The invention provides methods and compositions for controlling postoperative change in lower extremity length during total hip arthroplasty. The general method comprises determining a control distance between proximal and distal fixed reference points on a control femur, wherein the control distance provides an indication of and/or correlates with the length of the femoral head of the control femur, and adjusting a corresponding operative distance between corresponding proximal and distal fixed reference points on a corresponding operative femur of a lower extremity in relation to the control distance to control postoperative change in length of the lower extremity. In more particular embodiments, the proximal fixed reference point is at the center of rotation of the femoral head; the distal fixed reference point is at the tip of the greater trochanter; the control distance is measured along a line parallel with the axis of the control femur; the control femur is of a contralateral hip; the determining step is performed in reference to a radiograph of the control femur; the adjusting step minimizes a difference between the control and operative distances; and the adjusting step comprises the steps of installing on the operative femur a provisional femoral head and measuring the operative distance along the axis of the operative femur from a pin inserted into the axis of rotation of the provisional femoral head such that the axis of the pin is perpendicular to the axis of the operative femur to the greater trochanter of the operative femur. The invention also provides provisional femoral heads comprising a pin inserted into the axis of rotation of the head whereby when the head is installed on an operative femur, the axis of the pin is perpendicular to the axis of the femur, and the distance along the axis of the femur between the pin and the greater trochanter of the operative femur, provides a reproducible measurement useful for controlling postoperative change in lower extremity length during total hip arthroplasty. The invention also provides systems comprising a plurality of incrementally-sized such provisional femoral heads, wherein each head provides a different distance along the axis of the femur between the pin and the greater trochanter of the operative femur, femurs comprising such provisional femoral heads, etc.

DETAILED DESCRIPTION OF PARTICULAR EMBODIMENTS OF THE INVENTION

Figure 1:
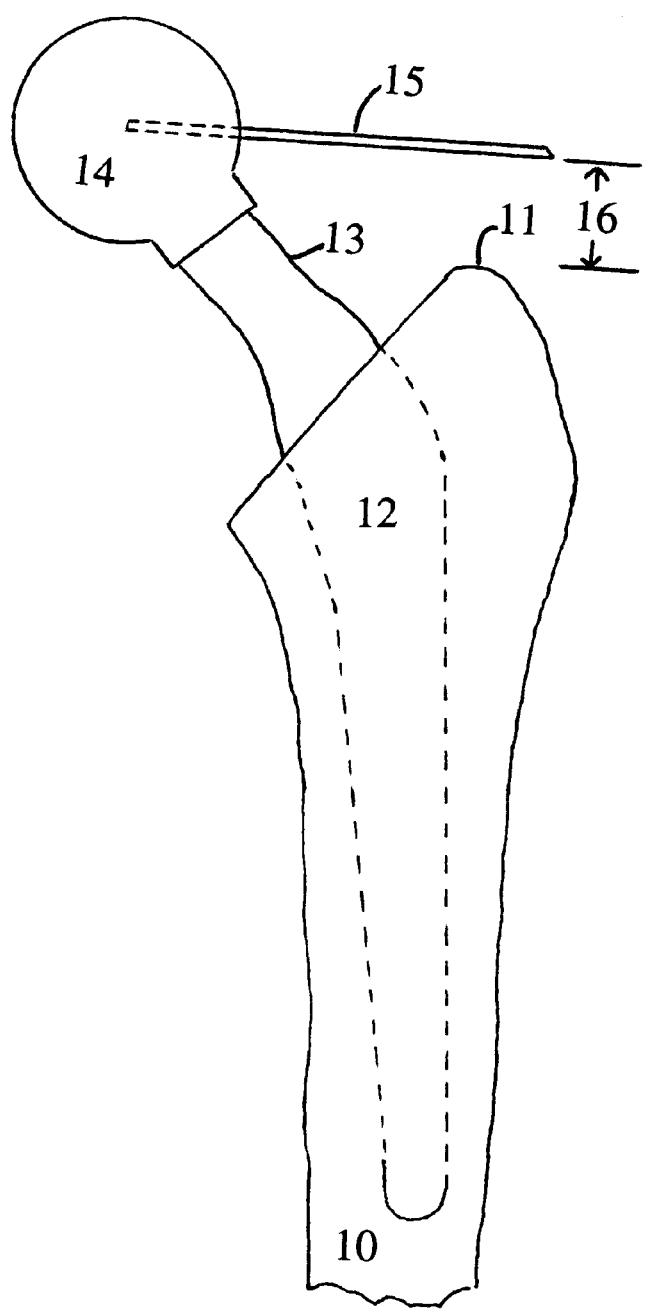
FIG. 1 shows a schematic of an operative femur with an affixed provisional femoral head.

The following descriptions of particular embodiments are offered by way of illustration and not by way of limitation.

We have found that in virtually all primary THA cases, the source of leg length inequality is the femoral component and that conventional hemispherical cementless acetabular (cup) implants do not substantially affect location of the joint center of rotation. Accordingly, rather than taking measurements which span across a ball and socket joint, the present invention simplifies measurements by considering the center of rotation of the artificial joint and using fixed reference points off of the femur only. Any reference points that consider the femoral head and neck components may be used. In a particular embodiment, the measured distance is taken along a line parallel to the long axis of the femur, between a first point off the center of rotation of the joint to a second fixed reference point on the femur. Any convenient second reference point, such as a point off the greater or lesser trochanter, may be used. Where the tip of the greater trochanter is used (preferred because of surgical exposure), we term this indicator of lower extremity length the "vertical drop measurement".

FIG. 1 shows a schematic of an operative femur 10 comprising a greater trochanter 11. Shown inserted into the intramedullary canal of the femur 10 is a femoral implant stem 12 and affixed onto the neck 13 of the stem 12, a provisional femoral head 14. Through the axis of rotation of the head is inserted a pin 15. The distance along the axis of the femur between the pin 15 and the greater trochanter 11, defines the vertical drop measurement 16 of the operative femur.

A control (non-operative) indicator measurement of lower extremity length is obtained by any convenient direct and indirect method. In one embodiment, a control distance is obtained as follows: preoperative radiographs are marked to determine the center of rotation of the contralateral unaffected hip (which may be a normal joint, or a previously replaced artificial hip). The center of the femoral head is accurately located using a template with concentric circles. The axis of the femoral shaft is drawn on the radiograph, and a perpendicular line from this axis is marked along the tip of the greater trochanter. The vertical distance between the perpendicular line and the center of the femoral head is recorded as the vertical drop measurement. The magnification factor (typically 15%) can be estimated with proportional scales.

The vertical drop distance of the operative femur may be obtained by a variety of ways. In one embodiment, a series of incrementally sized provisional femoral heads, each comprising a pin protruding from its center of rotation perpendicularly to the long axis of the femur and toward the greater trochanter. Measurement calipers are used to determined the vertical drop distance between the pin and a line off a fixed reference point of the femur, such as the top of the greater trochanter. In another embodiment, a jig which accounts for the bend of the femoral stem is attached to the trunion following femoral component implantation. The jig positions a rod parallel to the shaft of the femur since the femoral stem has previously been positioned within the intramedullary canal. The jig is attached to the trunion with a polyethylene sleeve which tightly fits onto the metallic trunion, without damaging the implant. A cross pin which slides along the rod can be lowered to the tip of the greater trochanter, permitting measurement of the "vertical drop". The rod and cross pin are removed from the jig, which is also removed from the trunion. When a trial femoral head is attached to the trunion, the center of the ball is marked by using a flat surface to which sterile ink has been applied. The flat ink surface is held parallel with the perspective used to read the perpendicular reference cross pin. The marked center is compared to the rod and cross pin which is repositioned along the tip of the greater trochanter. The vertical distance between the tip of the greater trochanter (the cross pin) and the center of the femoral head provides an accurate measurement of the length of the femur after insertion of the implant. This value can be compared with a similar measurement of the opposite hip on the preoperative radiograph to prevent excessive limb length discrepancy during THA procedures.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for controlling postoperative change in lower extremity length during total hip arthroplasty comprising steps:
    determining a control distance between proximal and distal fixed reference points on a control femur, wherein the control distance provides an indication of the length of the femoral head of the control femur,
    adjusting a corresponding operative distance between corresponding proximal and distal fixed reference points on a corresponding operative femur of a lower extremity in relation to the control distance to control postoperative change in length of the lower extremity.

2. The method of claim 1, wherein the proximal fixed reference point is at the center of rotation of the femoral head.

3. The method of claim 1, wherein the distal fixed reference point is at the tip of the greater trochanter.

4. The method of claim 1, wherein the control distance is measured along a line parallel with the axis of the control femur.

5. The method of claim 1, wherein the control femur is of a contralateral hip.

6. The method of claim 1, wherein the determining step is performed in reference to a radiograph of the control femur.

7. The method of claim 1, wherein the adjusting step minimizes a difference between the control and operative distances.

8. The method of claim 1, wherein the adjusting step comprises the steps of installing on the operative femur a provisional femoral head and measuring the operative distance along the axis of the operative femur from a pin inserted into the axis of rotation of the provisional femoral head such that the axis of the pin is perpendicular to the axis of the operative femur, to the greater trochanter of the operative femur.

9. A provisional femoral head comprising a pin inserted into the axis of rotation of the head whereby when the head is installed on an operative femur, the axis of the pin is perpendicular to the axis of the femur, and the distance along the axis of the femur between the pin and the greater trochanter of the operative femur, provides a reproducible measurement useful for controlling postoperative change in lower extremity length during total hip arthroplasty.

10. A system for controlling postoperative change in lower extremity length during total hip arthroplasty comprising a plurality of provisional femoral heads according to claim 9, wherein each head provides a different distance along the axis of the femur between the pin and the greater trochanter of the operative femur.

11. An operative femur comprising a provisional femoral head according to claim 9.

* * * * *